(12) United States Patent
Blanc

(10) Patent No.: US 10,639,054 B2
(45) Date of Patent: May 5, 2020

(54) LAPAROSCOPY FORCEPS

(71) Applicant: AB MEDICA, Mery-sur-Cher (FR)

(72) Inventor: Alexandre Blanc, Marseilles (FR)

(73) Assignee: AB MEDICA, Méry-sur-Cher (FR)

( * ) Notice: Subject to any disclaimer, the term of this patent is extended or adjusted under 35 U.S.C. 154(b) by 196 days.

(21) Appl. No.: 15/758,084

(22) PCT Filed: Aug. 22, 2016

(86) PCT No.: PCT/FR2016/000131
§ 371 (c)(1),
(2) Date: Mar. 7, 2018

(87) PCT Pub. No.: WO2017/042441
PCT Pub. Date: Mar. 16, 2017

(65) Prior Publication Data
US 2018/0242992 A1 Aug. 30, 2018

(30) Foreign Application Priority Data

Sep. 8, 2015 (FR) ..................................... 15 01851

(51) Int. Cl.
*A61B 17/29* (2006.01)
(52) U.S. Cl.
CPC ...... *A61B 17/29* (2013.01); *A61B 2017/2903* (2013.01); *A61B 2017/294* (2013.01); *A61B 2017/2933* (2013.01); *A61B 2017/2939* (2013.01); *A61B 2017/2941* (2013.01)
(58) Field of Classification Search
CPC ............ A61B 17/29; A61B 2017/2901; A61B 2017/2902; A61B 2017/2903; A61B 2017/2926; A61B 2017/2932; A61B 2017/2933; A61B 2017/2939; A61B 2017/294; A61B 2017/2941; A61B 2017/2944
See application file for complete search history.

(56) References Cited

U.S. PATENT DOCUMENTS

| 5,312,434 | A | 5/1994 | Crainich |
| 2010/0249700 | A1 | 9/2010 | Spivey |
| 2012/0203063 | A1 | 8/2012 | Suzuki et al. |

FOREIGN PATENT DOCUMENTS

| DE | 299 11 011 | 9/1999 |
| DE | 10 2011 001890 | 10/2012 |
| EP | 2 147 638 | 1/2010 |
| JP | 06 296619 | 10/1994 |

OTHER PUBLICATIONS

International Search Report, PCT/FR2016/000131; dated Nov. 21, 2016.

*Primary Examiner* — Melanie R Tyson
(74) *Attorney, Agent, or Firm* — Young & Thompson

(57) ABSTRACT

Disclosed are laparoscopy forceps, including a yoke with a hole, two jaws; a unit for mounting the jaws to pivot relative to the yoke about an axis; a control rod mounted to move in translation in the hole; a pantograph connecting the rod and two jaws using links mounted to pivot on the rod about an axis, two cams secured to the jaws, a mount for each link to pivot relative to a respective one of the two cams about axes, the four pivot axes being parallel, the outside diameter of the yoke being 2D, the width of the links being 2E, the distance between the axes when the two grip faces of the jaws are in contact being 2C, the angle under such circumstances between the axes being 2A, and the values D, E, C, and A being substantially associated by the following equation: $D = C + E/\cos A$.

16 Claims, 3 Drawing Sheets

LAPAROSCOPY FORCEPS

The present invention relates to laparoscopy forceps.

Laparoscopy is a minimally-invasive surgical technique for intervention and diagnostic purposes, in particular in human abdominal cavities such as the digestive system, and also for gynecological and urological purposes. It is performed by means of "laparoscopy forceps".

A general and diagrammatic view of such laparoscopy forceps is given in FIG. 1, which forceps are already known, e.g. as described and shown in documents U.S. Pat. No. 5,312,434 and DE 299 11 011.

Such forceps comprise a yoke having a through hole in the form of a circular cylinder defined between a proximal end and a distal end, two jaws having grip faces, means for mounting the two jaws at the distal end of the through hole to pivot relative to the yoke about a first axis so that the two jaws are suitable for occupying any position between two extreme positions, namely an open position when the two respective grip faces of the two jaws form between them a non-zero angle, and a closed position when the two respective grip faces of the two jaws form between them an angle that is substantially zero.

The forceps also include a control rod mounted to move in translation in the through hole and defined between a proximal end and a distal end, the proximal end being connected to means for controlling movement of the rod in translation in the yoke, e.g. of the type comprising a trigger or the like, as shown in FIG. 1.

In order to transform the movement in translation of the control rod into pivoting movements of the jaws, the forceps include pantograph-forming means that connect the distal end of the control rod to both of the jaws, respectively.

It is also known that such pantograph-forming means essentially comprise two links, means for mounting each of the two links via a first one of their two ends to the distal end of the rod, to pivot relative to the control rod and about a second axis, two cams, each secured to a respective one of the two jaws via a first one of its two ends, the longitudinal axes of the two cams forming between them a substantially zero angle when the two grip faces of the jaws are in contact, and means for mounting the second ends of each of the links to the second ends of the two cams to pivot about respective third and fourth axes, with the first, second, third, and fourth axes being defined so as to be parallel.

Such laparoscopy forceps give good results, but they can present drawbacks.

In particular, the forceps of U.S. Pat. No. 5,312,434 and DE 299 11 011 present a section of overall size that is greater than the outside diameter of the yoke, thereby leading to the drawback of providing a guide tube in which the yoke is engaged that has an inside diameter that is greater than the outside diameter of the yoke. Under such circumstances, the yoke is not well guided and the forceps can move laterally, thereby degrading the accuracy of the procedure.

Specifically, since the links are subjected to relatively large forces when the forceps are in use, it can happen relatively often that they break, thereby degrading the reliability of the forceps.

The present invention thus has the object of providing laparoscopy forceps that mitigate the above-mentioned drawbacks, but without being more expensive than prior art laparoscopy forceps, and having a structure that satisfies the following two opposing conditions: being compact so as to be capable of being inserted in human cavities via a guide tube of limited through diameter, and being of maximum strength for performing the desired operation, e.g. ablating a diseased body element, while avoiding any in situ breakage of any of the component elements of the forceps.

More precisely, the present invention provides laparoscopy forceps comprising at least:
- a yoke having an outside diameter that is constant over its entire functional length defined between its proximal end and its distal end and having a circularly cylindrical through hole defined between said proximal and distal ends;
- two jaws having respective grip faces;
- means for mounting the two jaws to the distal end of said through hole to pivot relative to said yoke about a first axis in such a manner that the two jaws are suitable for occupying all positions between two extreme positions, respectively an open position when the two grip faces of the respective jaws form a non-zero angle between each other, and a closed position when the two grip faces of the respective jaws form a substantially zero angle between each other;
- a control rod mounted to move in translation in said through hole and defined between a proximal end and a distal end; and
- pantograph-forming means for connecting the distal end of said control rod respectively to both of said jaws, said pantograph-forming means comprising:
  - two links;
  - means for mounting said two links via respective first ones of their two ends to the distal end of said rod to pivot relative to the control rod about a second axis;
  - two cams secured to respective ones of the two jaws at first ones of their two ends; and
  - means for mounting the second end of each link to the second end of a respective one of the cams to pivot respectively about a third axis and a fourth axis, said first, second, third, and fourth axes being defined so as to parallel, the forceps being characterized by the facts that:
the outside diameter of said yoke has a value equal to 2D;
the links are identical, each being formed by a plate of rectangular cross-section with rounded ends, the width of said plate being equal to 2E;
the distance between the third and fourth pivot axes when the two grip faces of the jaws are in contact having a value 2C that is less than 2D; and
the angle between the axes of two links when the two grip faces of the jaws are in contact being equal to 2A;
the values D, E, C, and A being substantially associated by the following equation:

$$D = C + E/\cos A$$

and that:
the outer edge at the second end of each link has a substantially chamfered cylindrical portion of radius substantially equal to the radius of the outer surface of said yoke so that, when the two jaws are in the closed position, said pantograph-forming means are inscribed in and against the envelope surface defined by said outer surface of said yoke.

Other characteristics and advantages of the invention appear from the following description given with reference to the accompanying drawings by way of non-limiting illustration, in which.

Figure 1:
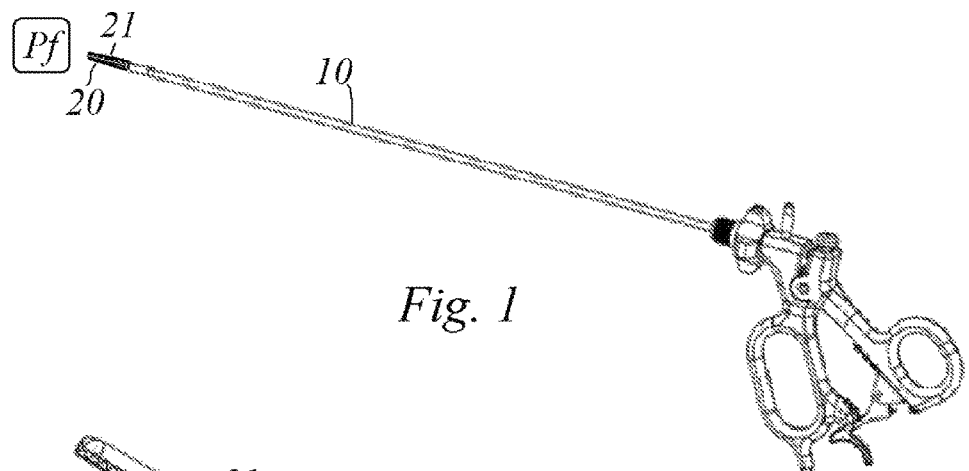
FIG. 1 is an overall view of laparoscopy forceps, both of the prior art and of the invention.
Figure 5:
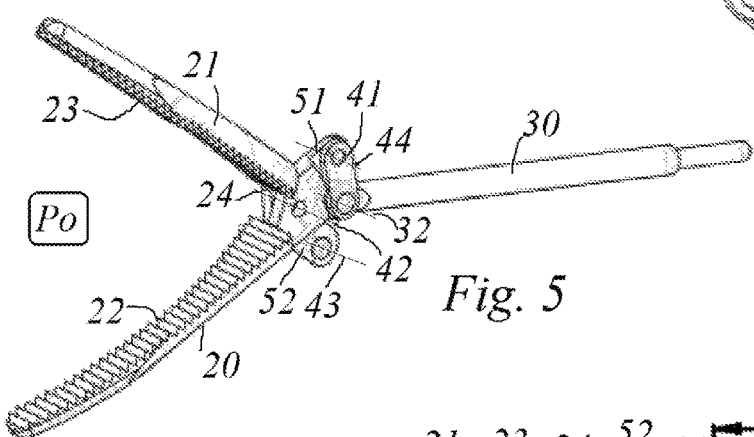
Figure 3:
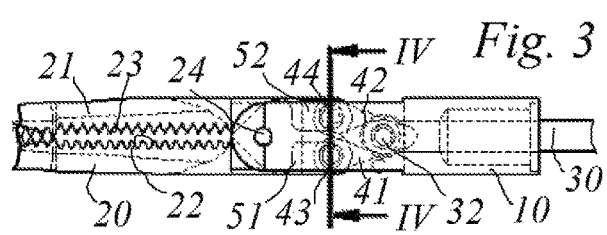
Figure 4:
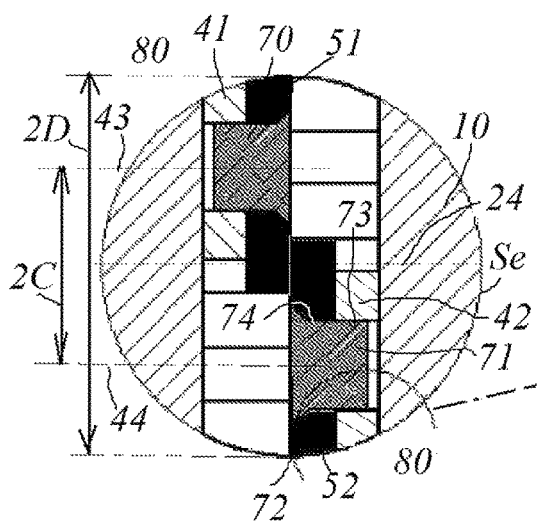
Figure 4:
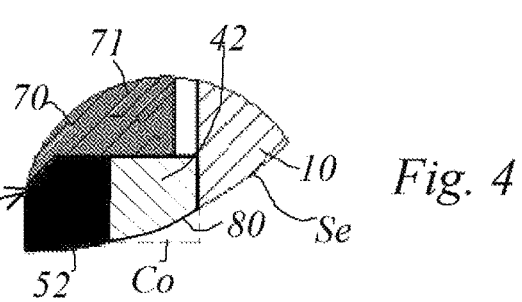
Figure 2:
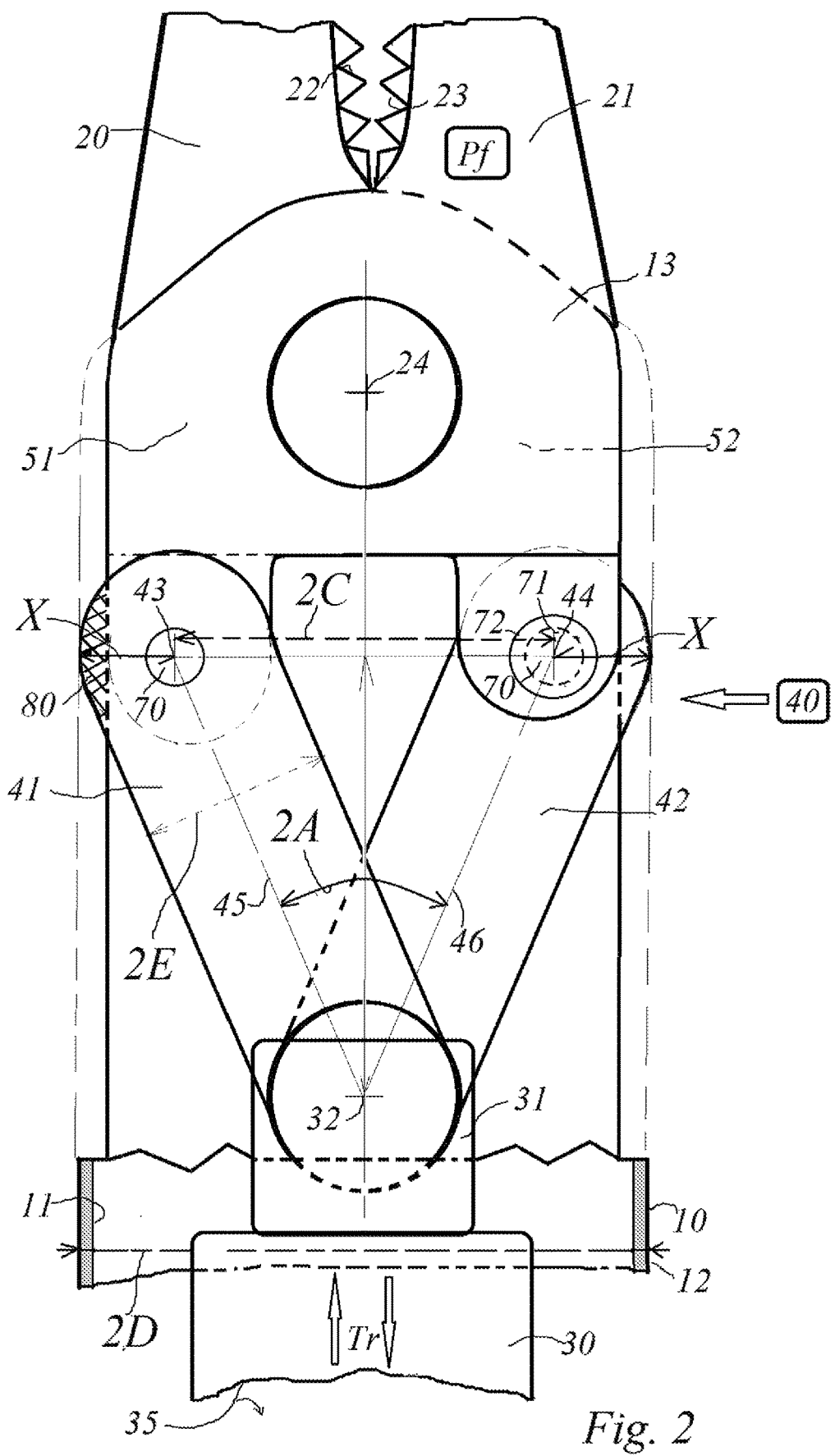
FIG. 2 is a partially-cutaway diagrammatic theoretical view of a portion of laparoscopy forceps in accordance with the present invention.
Figure 6:
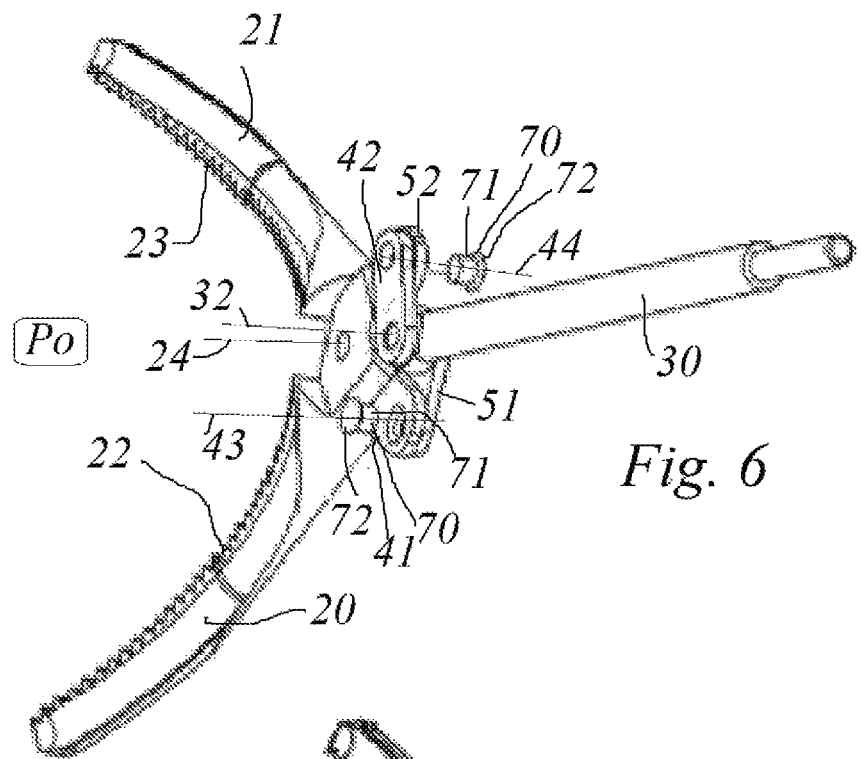
Figure 7:
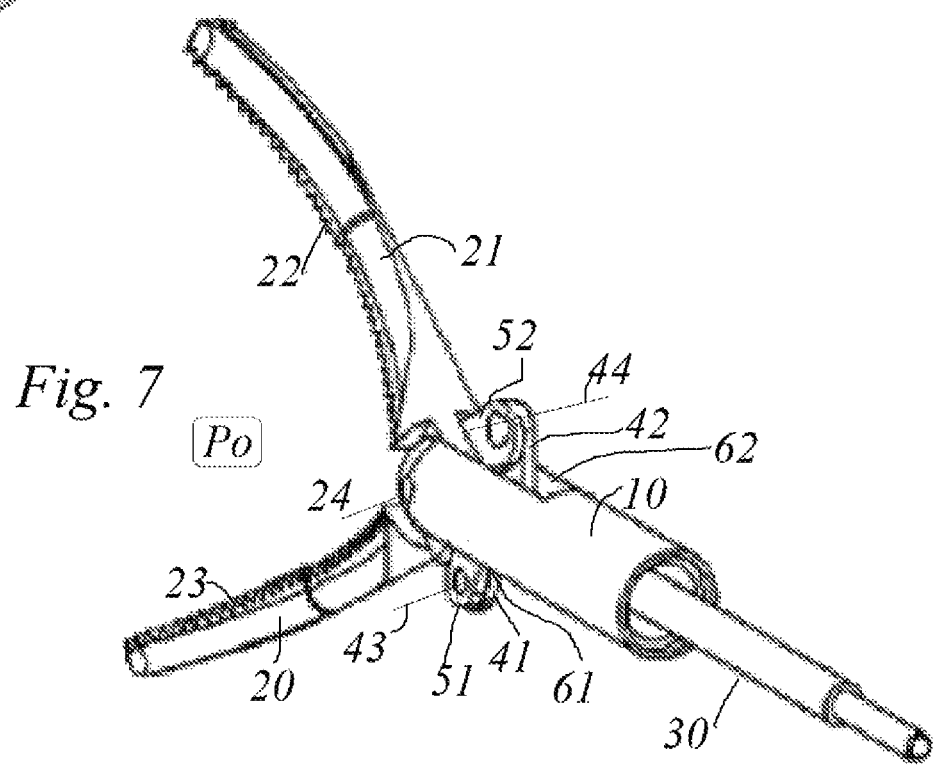

FIGS. 3 and 4 show respectively, for FIG. 3: a diagrammatic longitudinal section view of the portion of the industrial laparoscopy forceps of the invention as shown in FIG. 2, which is a view of the same portion on a scale that is larger than that of FIG. 3, and for FIG. 4: a cross-section view referenced IV-IV in FIG. 3, together with a detail view of a portion that is ringed in FIG. 4, so as to show clearly a characteristic of the invention; and FIGS. 5, 6, and 7, show in agreement with FIGS. 1 to 4, three different isometric perspective views serving to make it easy to understand the structure of the laparoscopy forceps of the invention.

It is specified initially that in the present description if the adverb "substantially" is associated with a qualification for any given means, and without any further details, then that qualification should be understood either strictly or approximately.

With reference to all of the figures, the present invention relates to laparoscopy forceps comprising at least a yoke 10 having an outside diameter that is constant over its functional length defined between its proximal end 12 and its distal end 13, and further including a circularly cylindrical through hole 11 defined between its proximal end 12 and its distal end 13, such a yoke generally and most advantageously being constituted by a circularly cylindrical tube.

The forceps also comprise two yaws 20 and 21 having grip faces 22 and 23, that are optionally serrated, as shown.

The term "grip face" should be understood in the meaning of the present description to cover any surface that is suitable for coming into contact with a given body, e.g. for the purpose of: taking hold of it, crushing it, cutting it, amputating it, etc.

The forceps also include means for mounting the two jaws at the distal end 13 of the through hole 11 to pivot relative to the yoke about a first axis 24 so that these two jaws can occupy any position between two extreme positions, namely an open position Po when the grip faces of the two respective jaws form between them a non-zero angle, and a closed position Pf (FIGS. 1, 2, and 3), when the two grip faces respectively of the two jaws form between them an angle that is substantially zero.

A control rod 30 is also provided that is mounted to be moveable in translation Tr in the through hole 11 and that is defined between a proximal end 35 and a distal end 31, the proximal end of the control rod 30 being coupled to means of trigger or analogous type in order to control movement in translation in both directions of the control rod inside the yoke in both directions. These means are themselves well known and they are not described in greater detail herein, solely for the purpose of simplifying the present description.

Pantograph-forming means 40 are also provided for connecting the distal end 31 of the control rod respectively to both of the jaws, as can seen more particularly in FIG. 2. In known manner, these pantograph-forming means comprise two links 41 and 42, means for mounting both of the two links via respective first ones of their two ends to the distal end 31 of the rod 30 to pivot relative to the control rod about a second axis 32, and two cams 51 and 52 secured respectively to the two jaws 20 and 21, each via a first one of its two ends.

These pantograph means further comprise means for mounting the second end of each link 41, 42 to the second end of a respective cam 51, 52 to pivot respectively about a third axis 43 or a fourth axis 44.

It is also specified that these first, second, third, and fourth axes 24, 32, 43, and 44 are all mutually parallel.

According to an essential characteristic of the invention, given that:

the outside diameter of the yoke 10 has a value equal to 2D;

the links 41 and 42 are identical, each being formed by a plate of rectangular cross-section with a rounded or equivalent end, see for example FIG. 2, with the width of the plate being equal to 2E;

the distance between the third and fourth pivot axes 43 and 44 when the two grip faces 22 and 23 of the jaws 20 and 21 are in contact has a value 2C that is less than 2D; and the value of the angle between the axes 45 and 46 of the two links 41 and 42 when the two grip faces of the jaws are in contact is equal to 2A, then the values D, E, C, and A are substantially associated by the following equation:

$$D = C + E/\cos A$$

The value of cos A (the cosine of the angle A) is determined by the ratio Z/Y where:

Y is the distance between the second axis 32 and either one of the third and fourth axes 43 and 44; and Z is the distance between the first axis 32 and the straight line passing through the third and fourth axes 43 and 44, when the grip faces 22 and 23 are in contact.

It is specified that the term "substantially associated by the following equation" means that the value "C+E/cos A" may be exactly equal to D or very slightly less, in particular because of the "rounded" shape of the ends of the links.

In addition, since the links are made out of plates of rectangular section, one of their corners Co, corresponding to the outer edges of their second ends, as shown in the detailed portion of FIG. 4, projects from the outer surface Se of the yoke 10 and prevents the forceps from being inserted into the guide tube.

Furthermore, in order to enable the forceps to be caused to slide in the guide tube, the outer edges of the second ends of each of the links have respective substantially chamfered cylindrical portions 80 of radius substantially equal to the radius of the outer surface Se of the yoke 10 so that when the two jaws 20 and 21 are in the closed position Pf, the pantograph-forming means 40 are inscribed in and on the envelope surface defined by the outer surface Se.

Thus, this chamfered portion 80 can be caused to slide without difficulty over the inside surface of the guide tube when the forceps are inserted into the guide tube.

It is entirely possible for this chamfer to be made while weakening the link very little, and without in any way weakening the assembly between the links and the cams by means of pegs 70, as described below.

According to another characteristic of the invention that is important and preferred, the two cams 50 and 51 are situated between the two links 41 and 42.

In addition, the means for mounting the second end of a link 41, 42 on the second end of a cam 51, 52 are constituted by a respective peg 70 having a peg shank 71 and a shoulder-forming head 72 secured to the peg shank 71, with two circularly cylindrical orifices 73 and 74 being formed on a common axis respectively in the link and in the cam, the cross-sections of these orifices being substantially complementary to the cross-section of the peg shank 71 so that it can be slidably inserted in the two orifices, the peg also being engaged in these two orifices in such a manner that the shoulder-forming head 72 comes into contact with the face of the cam that faces towards the other cam, and means for securing the peg shank 71 with the respective link 41, 42 only.

These means for securing the peg shank 71 with the respective link 41, 42 only are selected from among the following means: welding, brazing, adhesive, and preferably welding when the materials used for making the links 41, 42 and the pegs 70 make that possible. These materials are thus preferably made of stainless steel or the like.

Most advantageously, the yoke 10 includes two open-ended slots 61 and 62 in the wall of its distal end 13, which slots are arranged so as to allow the connected-together ends of the two links 41, 42 and of the two cams 51, 52 to pass when the jaws 20 and 21 go from the closed position Pf to the open position Po, see for example the illustrations in FIGS. 5, 6, and above all FIG. 7.

In use, the forceps need to be inserted in a guide tube (not shown). The structure of the forceps of the invention makes it possible to provide a guide tube that has a cylindrical longitudinal through hole of a diameter that is substantially equal to the outside diameter 2D of the yoke 10 and advantageously very slightly greater, just enough to allow the yoke of the forceps to slide in the guide tube.

The overall transverse size of the two jaws 20 and 21 as defined in the plane of FIG. 2 can be seen to be smaller than the overall size of the two links. However these two overall sizes can be advantageously substantially identical and thus substantially equal to the outside diameter of the yoke 10, as shown in FIGS. 3 and 4.

From the above description, it can be seen in particular that the links may in any event have a maximum width for a given application that is greater than the widths of prior art laparoscopy forceps, which can but impart greater reliability to the forceps of the invention, in particular by avoiding potential breakage of the links, which absorb a maximum amount of force when the forceps are used in laparoscopy.

The invention claimed is:

1. Laparoscopy forceps comprising at least:
   a yoke having an outside diameter that is constant over its entire functional length defined between its proximal end and its distal end and having a circularly cylindrical through hole defined between said proximal and distal ends;
   two jaws having respective grip faces;
   means for mounting the two jaws to the distal end of said through hole to pivot relative to said yoke about a first axis in such a manner that the two jaws are suitable for occupying all positions between two extreme positions, respectively an open position when the two grip faces of the respective jaws form a non-zero angle between each other, and a closed position when the two grip faces of the respective jaws form a substantially zero angle between each other;
   a control rod mounted to move in translation in said through hole and defined between a proximal end and a distal end; and
   pantograph-forming means for connecting the distal end of said control rod respectively to both of said jaws, said pantograph-forming means comprising:
      two links;
      means for mounting said two links via respective first ones of their two ends to the distal end of said rod to pivot relative to the control rod about a second axis;
      two cams secured to respective ones of the two jaws at first ones of their two ends; and
      means for mounting the second end of each link to the second end of a respective one of the cams to pivot respectively about a third axis and a fourth axis, said first, second, third, and fourth axes being defined so as to be parallel to one another,
   wherein:
      the outside diameter of said yoke has a value equal to 2D;
      the two links are identical, each being formed by a plate of rectangular cross-section with rounded ends, the width of each plate being equal to 2E;
      the distance between the third and fourth pivot axes when the two grip faces of the jaws are in contact having a value 2C that is less than 2D; and
      the angle between the axes of the two links when the two grip faces of the jaws are in the closed position being equal to 2A;
      the values D, E, C, and A being substantially associated by the following equation:

$$D = C + E/\cos A$$

and that:
      the outer edge at the second end of each link has a substantially chamfered cylindrical portion of radius substantially equal to the radius of the outer surface of said yoke so that, when the two jaws are in the closed position, said pantograph-forming means are inscribed in and against an envelope surface defined by said outer surface of said yoke.

2. Laparoscopy forceps according to claim 1, wherein the two cams are situated between the two links.

3. Laparoscopy forceps according to claim 2, wherein the means for mounting the second end of each link to pivot relative to the second end of each cam are constituted by:
   a peg comprising a peg shank and a shoulder-forming head secured to said peg shank;
   two circularly cylindrical orifices on a common axis respectively in each link and in each cam, the cross-section of said orifices being substantially complementary to the cross-section of said peg shank so that the shank can be engaged slidably in the two orifices, said peg being engaged in the two orifices in such a manner that said shoulder-forming head is in contact with each cam; and
   means for securing said peg shank to each link.

4. Laparoscopy forceps according to claim 3, wherein means for securing said peg shank to said each link are selected from the following means: welding; brazing; adhesive.

5. Laparoscopy forceps according to claim 4, wherein the yoke includes, in its distal end, two open-ended slots arranged so as to pass the connected-together ends of the two links and the two cams when the jaws go from the closed position to the open position.

6. An assembly, comprising laparoscopy forceps according to claim 5 and a guide tube having a cylindrical longitudinal through hole of diameter substantially equal to the outside diameter of said yoke.

7. An assembly, comprising laparoscopy forceps according to claim 4 and a guide tube having a cylindrical longitudinal through hole of diameter substantially equal to the outside diameter of said yoke.

8. Laparoscopy forceps according to claim 3, wherein the yoke includes, in its distal end, two open-ended slots arranged so as to pass the connected-together ends of the two links and the two cams when the jaws go from the closed position to the open position.

9. An assembly, comprising laparoscopy forceps according to claim 8 and a guide tube having a cylindrical longitudinal through hole of diameter substantially equal to the outside diameter of said yoke.

10. An assembly, comprising laparoscopy forceps according to claim 3 and a guide tube having a cylindrical longitudinal through hole of diameter substantially equal to the outside diameter of said yoke.

11. Laparoscopy forceps according to claim 2, wherein the yoke includes, in its distal end, two open-ended slots arranged so as to pass the connected-together ends of the two links and the two cams when the jaws go from the closed position to the open position.

12. An assembly, comprising laparoscopy forceps according to claim 11 and a guide tube having a cylindrical longitudinal through hole of diameter substantially equal to the outside diameter of said yoke.

13. An assembly, comprising laparoscopy forceps according to claim 2 and a guide tube having a cylindrical longitudinal through hole of diameter substantially equal to the outside diameter of said yoke.

14. Laparoscopy forceps according to claim 1, wherein the yoke includes, in its distal end, two open-ended slots arranged so as to pass the connected-together ends of the two links and the two cams when the jaws go from the closed position to the open position.

15. An assembly, comprising laparoscopy forceps according to claim 14 and a guide tube having a cylindrical longitudinal through hole of diameter substantially equal to the outside diameter of said yoke.

16. An assembly, comprising laparoscopy forceps according to claim 1 and a guide tube having a cylindrical longitudinal through hole of diameter substantially equal to the outside diameter of said yoke.

\* \* \* \* \*